United States Patent [19]

Günther et al.

[11] 4,001,221
[45] Jan. 4, 1977

[54] 4-STILBENYL-5-CYANO-1,2,3-TRIAZOLES

[75] Inventors: Dieter Günther; Hans Jürgen Nestler, both of Kelkheim, Taunus; Günter Rösch, Altenhain, Taunus; Erich Schinzel, Hofheim, Taunus, all of Germany

[73] Assignee: Hoechst Aktiengesellschaft, Frankfurt am Main, Germany

[22] Filed: Sept. 12, 1975

[21] Appl. No.: 612,700

[30] Foreign Application Priority Data

Sept. 13, 1974 Switzerland ............... 12469/74

[52] U.S. Cl. ............. 260/240 C; 260/240 D; 260/308 A
[51] Int. Cl.² ............. C07D 249/04; C07D 249/06; C07D 413/04
[58] Field of Search .... 260/308 A, 240 CA, 240 C, 260/240 D, 240

[56] References Cited
UNITED STATES PATENTS 3,470,196   9/1969   Harvey .................. 260/308 A
3,928,373  12/1975   Beck et al. ............ 260/240 CA X

OTHER PUBLICATIONS

N. S. Zefirov et al., "Rearrangements and Cyclizations 11, Reaction of α, β,-Unsaturated Nitriles with Sodium Azide", pp. 2605–2608.

*Primary Examiner*—Allen B. Curtis
*Attorney, Agent, or Firm*—Connolly and Hutz

[57] ABSTRACT

Compounds of the formula (I)

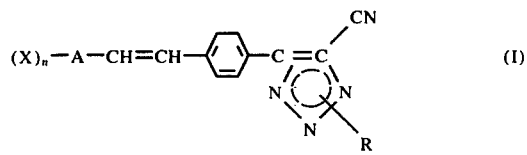

in which R is hydrogen, or lower alkyl, which may be substituted by phenyl, hydroxy, lower carbalkoxy or cyano, X is hydrogen, chlorine, methyl, methoxy, cyano or lower carbalkoxy, n is 1 to 3, and A is an aromatic carboxylic group or an aromatic hetero-cyclic 5- or 6-membered group as well as their N-alkylated quaternary reaction products. These compounds are useful as optical brighteners for lacquers, natural or synthetic fibers and films, foils or other shaped forms made therefrom.

9 Claims, No Drawings

4-STILBENYL-5-CYANO-1,2,3-TRIAZOLES

The present invention relates to 4-stilbenyl-5-cyano-1,2,3-triazoles, their preparation and their use as optical brighteners for natural and synthetic substrates.

In the hitherto known 4-stilbenyl-1,2,3-triazoles, the N-atom 2 always carries a group such as a phenyl, substituted phenyl or naphthyl group, or other aromatic substituents by which the conjugation is prolonged or extended (JA-OS 73/20406, German Offenlegungsschrift 2,062,383 and 2,262,340).

Now, we have found that 5-cyano-1,2,3-triazoles which contain, in the 4-position, an aromatic radical linked over a styryl bridge and which do not carry substituents at the ring nitrogen atoms extending the conjugation, are suitable as optical brighteners or fluorescent dyestuffs. The above-mentioned aromatic radical encompasses a continuous system of conjugated double linkages standing in conjugation with the ethylidene group to which the aromatic radical is bound.

Hence, the present invention provides compounds of the general formula (I)

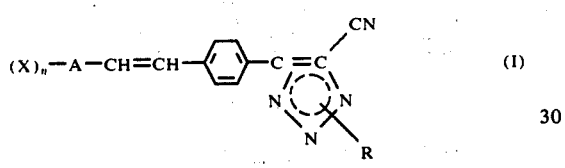
(I)

in which

R represents a hydrogen atom, or a lower alkyl group, which may be substituted by a phenyl, hydroxy, lower carbalkoxy or cyano group, A represents an aromatic carbocyclic radical consisting of 1 to 4 annelated benzene nuclei or benzene nuclei which are linearly linked directly or over an ethylidene group, or an aromatic heterocyclic 5- or 6-membered radical which contains up to 3 hetero-atoms from the series of oxygen, nitrogen and sulfur atoms and which may be annelated to a benzene or naphthalene radical and/or linked over a phenylene radical, X represents hydrogen atoms or identical or different non-chromophorus radicals of the series of fluorine, chlorine or bromine atoms, lower alkyl, lower alkoxy, amino, lower mono- or di-alkyl amino, lower trialkyl ammonium, acyl amino groups, or carboxy or sulfo groups which may be functionally modified, and 2 adjacent radicals X may together also represent a lower alkylene or an 1;3-dioxaproplene group, and $n$ represents 1 to 3.

Those compounds of the formula (I) are preferred in which R represents a hydrogen atom or a methyl or ethyl group, A represents a radical of the formula

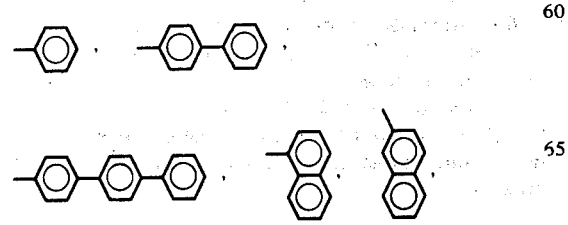

-continued

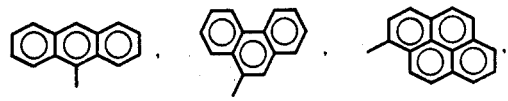

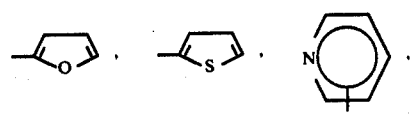

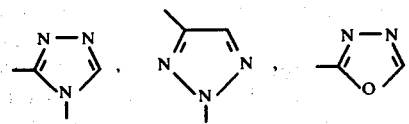

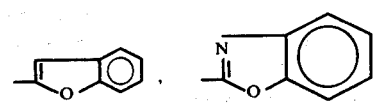

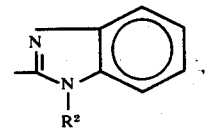

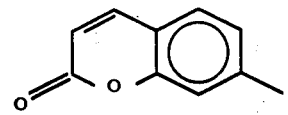

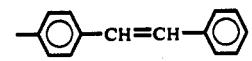

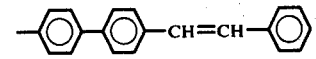

or

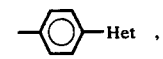

wherein Het has the following meaning:

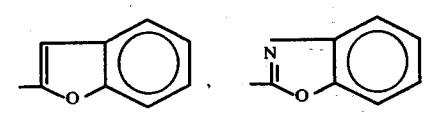

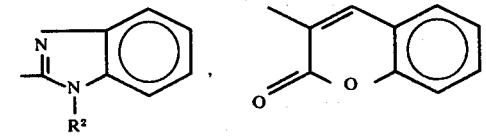

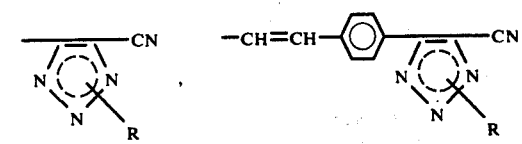

or

-continued

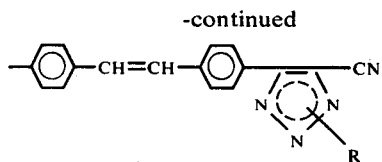

and R¹ represents a hydrogen atom, a lower alkyl group or the phenyl group,

And R² represents a hydrogen atom or a lower alkyl group, X represents a hydrogen, fluorine, chlorine or bromine atom, a lower alkyl, lower alkoxy, amino, lower mono- or dialkyl-amino, lower trialkyl-ammonium, lower alkanoylamino or benzoylamino group or a carboxy or sulfo group which may be functionally modified, and n is a number from 1 to 3.

Of particular interest are compounds of the formula (I), in which R represents a hydrogen atom or a methyl or ethyl group, A represents a group of the formula

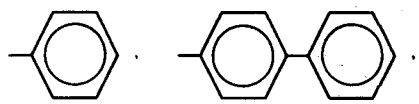

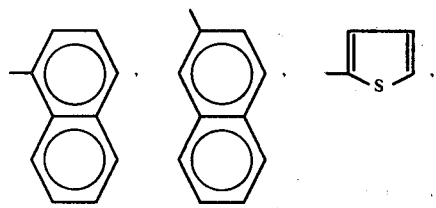

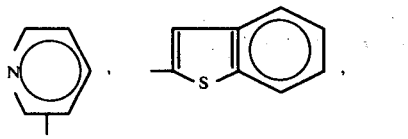

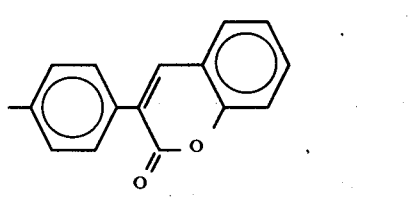

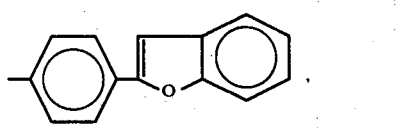

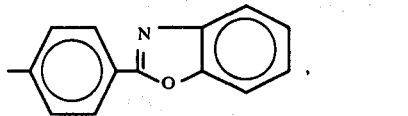

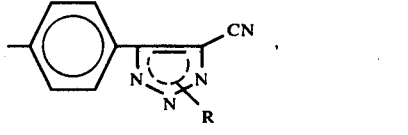

-continued

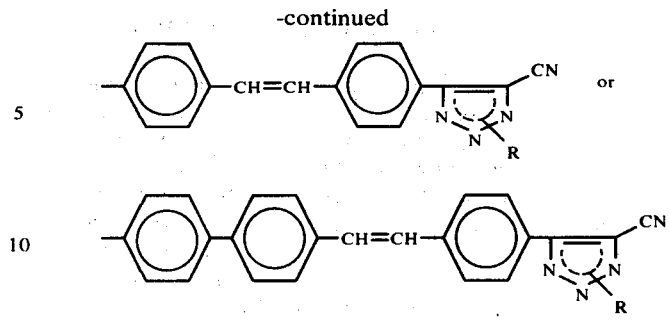

X represents hydrogen or chlorine atoms, methyl, methoxy, cyano, carboxy, lower carbalkoxy, amino, lower mono- or dialkyl-amino or lower alkanoyl-amino or benzoyl-amino groups, and n is 1 to 3.

Particularly preferred as optical brighteners are the compounds of the formula (I), in which A represents a group of the formula

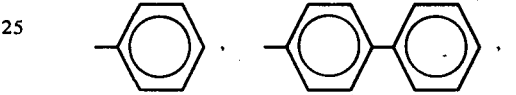

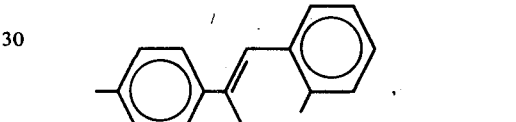

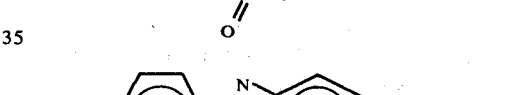

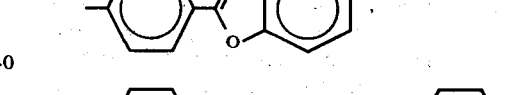

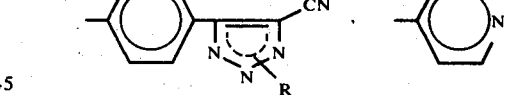

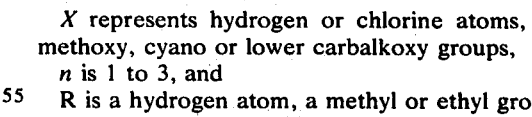

$X$ represents hydrogen or chlorine atoms, methyl, methoxy, cyano or lower carbalkoxy groups, n is 1 to 3, and R is a hydrogen atom, a methyl or ethyl group.

If, in connection with aliphatic radicals, the term "lower" or "low molecular" is used it shall denote rests containing up to 6, preferably up to 4, and in particular up to 2, carbon atoms.

"Functionally modified" carboxy groups comprise compounds in which 1 carbon atom has 3 linkages to hetero atoms, thus in the first instances the salts, preferably the alkali metal salts, alkaline earth metal salts, the aluminium and ammonium salts, but in particular the sodium, potassium and ammonium salts of the formula $H_3NY_{4-x}$ in which Y represents a lower alkyl group which may be substituted by hydroxy groups, and x represents a number from 1 to 4.

Furthermore, this term encompasses carboxylic acid esters, in particular phenyl esters and above all lower alkyl esters, the lower alkyl radicals of which may be substituted by hydroxy, lower alkoxy, lower dialkylamino or lower trialkyl -ammonium groups and the phenyl group may be substituted by halogen atoms, lower alkyl or lower alkoxy groups.

"Functionally modified" carboxy groups are furthermore the acid amides and acid hydrazides, the nitrogen atoms of which may be substituted by lower alkyl groups which themselves may be substituted by hydroxy, lower alkoxy, lower dialkylmino or trialkyl ammonium groups, or two of such lower alkyl groups together may form a saturated bivalent group, preferably, together with the nitrogen atom to which they are bound, the pyrrolidino, piperidino, hexamethylenimino, morpholino or piperazino radical.

"functionally modified" carboxy group is also the cyano group.

For "functionally modified" sulfo groups, the above indications shall apply in corresponding manner, i.e. with regard to the salts, esters and amides.

It has to be understood that the groups falling under the definitions of the symbols R,Z,A,X and n may be combined one with another, but that such subgeneric language is by no means intended to introduce new matter according to 35 U.S.C. 132.

The manner in which the triazole ring in formula I is illustrated shows that the positions of the hydrogen atoms or of the alkyl groups are not determined. In general, they are mixtures of the various tautomeric or isomeric forms (T. L. Gilchrist and G. E. Gymer, Adv. Heterocycl. Chem. 16, 33 (1974); c.f. also Y. Tanaka, S. R. Velen and S. L. Miller, Tetrahedron 29, 3271 (1973) and Y. Tanaka and S. I. Miller, Tetrahedron 29, 3285 (1973)).

The compounds of the formula (I) are prepared by the addition of sodium azide on arylsulfonylethylidene compounds (Chem. Ber. 106 (1973) 2758; German Offenlegungsschrift 2.138.522). This process is characterized by that, as the arylsulfonyl compound, a compound of the formula (II)

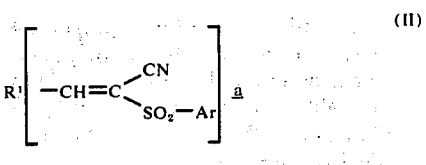

is reacted with a mole sodium azide, a being 1 or 2 and correspondingly $R^1$ being

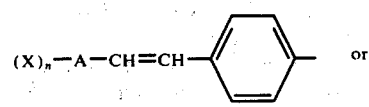

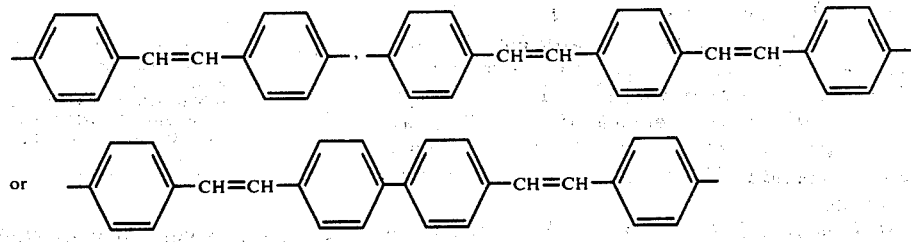

and Ar represents a phenyl group which may be substituted by fluorine, chlorine or bromine atoms, lower alkyl, lower alkoxy, nitro or lower alkanoylamino groups, or a compound of the formula (III)

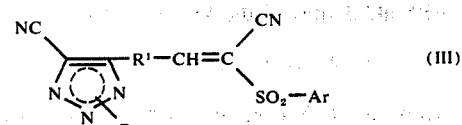

is reacted with 1 mole of sodium azide and in each case the radical R, if it is hydrogen, may be transformed partially or completely by alkylation into another radical R.

The reaction of the compound of the formula (II) or (III) with sodium azide is carried out in polar solvents, preferably dimethyl sulfoxide, lower alkanols, acetonitrile, hexamethylphosphoric acid trisamide and in particular dimethylformamide at temperatures in the range of from 0° to 200° C, preferably 20° to 155° C, in particular 60° to 100° C.1 to about 1.2 mole of sodium azide are used for each sulfonyl group.

The pre-products of the formulae (II) and (III) can be obtained according to known methods in the following ways:

Compounds of the formula (II) and correspondingly also those of the formula (III) may be prepared as follows:

In the above formulae, $R^1$, a and Ar have the above meaning and $R^2$ represents a formyl group (condensation according to KNOEVE-NAGEL) or a group of the formula

—CH=NR³

(condensation according to German Auslegeschrift 1,768,868), in which $R^3$ represents an organic radical which is bound to the nitrogen atom over a tert. carbon atom. With a view to the resulting product of the formula (II) and the final product of the formula (I), this radical is not critical and it is suitable to select a tert. butyl or a chlorophenyl group, in particular the phenyl group, for this purpose. The condensation according to KNOEVENAGEL is effected in a solvent serving as "water-dragger" (a solvent with forms with water an azeotrope which is easily decomposable), preferably an aromatic hydrocarbon, in particular benzene, toluene, or xylene or in mixtures of such solvents, if necessary with the addition of polar solvents such as dimethyl formamide or dimethyl sulfoxide as solubilizers. In general, stoichiometrical quantities of the reactants are used, if necessary an excess of aldehyde may be used. The reaction is carried out in general at normal pressure in the boiling solvent, thus at about 80° to about 150° C with addition of catalytical amounts of piperidine or a piperidine salt, for example the acetate or a mixture of piperidine or acetic ester, or also ammonium acetate.

Another method consists in reacting compounds of the formula

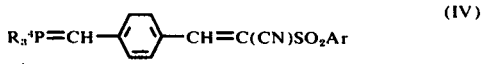

with aldehydes of the formula (VI)

$(X)_n—A—CHO$          (V)

according to Wittig, in which formulae Ar, X, A and N have the meanings given above and $R^4$ represents a cyclohexyl or, preferably a phenyl radical. This is also true in analogous manner for the dialdehydes of the formulae

which may be reacted with 2 moles of ylide (IV).

The compounds of the formula (IV) may be obtained according to the following reaction scheme:

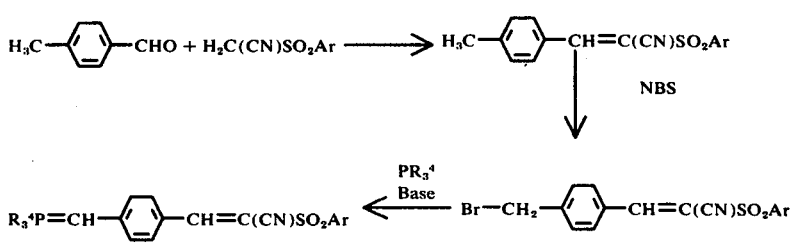

In this formulae, Ar and $R^4$ have the meanings given above, NSB denotes N-bromosuccinimide.

This reaction is suitably carried out as follows:

The bromomethyl compound is dissolved or suspended in a diluting agent such as chloroform or benzene, the phosphine $PR_3^4$ is added and the salt so obtained is reacted in a polar solvent such as dimethyl formamide, dimethyl sulfoxide or hexamethylene phosphoric acid tris-amide with a suitable base such as a lower alkali metal alkanolate, under the protection of an inert gas to yield the ylide. The aldehyde which may be dissolved in a polar solvent is then introduced in the ylide solution or suspension so obtained and the Wittig olefination is carried out at temperatures of about 60° to about 155° C. The 4-stilbenyl-5-cyano-1,2,3-triazoles of the formula (I) show in solid and dissolved state a strong and in many cases a very distinct reddish blue fluorescence. The new compounds may be used as optical brighteners in particular in admixture with other products which show for example a greenish blue fluorescence.

The absorption may be shifted to longer wave lengths by suitable substituents in the stilbene portion of the compounds of the formula (I), for example with

---

$(X)_nA$ = 2-methoxy-naphth-1-yl
            4-methoxy-naphth-1-yl
            4-N,N-dimethylaminophenol
            4'-(5-cyano-1,2,3,-[H]-triazole-4-yl)-stilbene-4-yl
            4'-[4'-(5-cyano-1,2,3-[H]-triazole-4-yl)-stilbene-4-yl]-phenyl

--- in such a manner that dyestuffs showing a greenish yellow fluorescence are obtained. Also with these products the alkylation of the triazole rings is possible in order to vary the optical and other properties required for utilization.

As optical brighteners, in particular the following new compounds of the formula (I) are suitable:

a. 4-(stilbene-4-yl)-5-cyano-1,2,3-[H]-triazole
b. 4-(4'-methyl-stilbene-4-yl)-5-cyano-1,2,3-[H]-triazole
c. 4-(4'-methoxy-stilbene-4-yl)-5-cyano-1,2,3-[H]-triazole
d. 4-(3',4',5'-trimethoxy-stilbene-4-yl)-5-cyano-1,2,3-[H]-triazole
e. 4-(3'-chloro-stilbene-4-yl)-5-cyano-1,2,3-[H]-triazole
f. 4-(4'-chloro-stilbene-4-yl)-5-cyano-1,2,3-[H]-triazole
g. 4-(4'-methoxycarbonyl-stilbene-4-yl)-5-cyano-1,2,3-[H]-triazole
h. 4-(4'-cyano-stilbene-4-yl)-5-cyano-1,2,3-[H]-triazole
i. 4-(4'-phenyl-stilbene-4-yl)-5-cyano-1,2,3-[H]-triazole
j. 4-[4'-(cumarine-3-yl)-stilbene-4-yl]-5-cyano-1,2,3-[H]-triazole
k. 4-[4'-(benzoxazole-2-yl)-stilbene-4-yl]-5-cyano-1,2,3-[H]-trizole
i. 4,4'-bis-(5-cyano-1,2,3-[H]-triazole-4-yl)-stilbene
m. 1-(pyride-4-yl)-2-[4(5-cyano-1,2,3-[H]-triazole-4-yl)-phenyl]-ethylene n. 1-(thiophene-2-yl)-2-[4-(5-cyano-1,2,3-[H]-triazole-4-yl)-phenyl]-ethylene o. 1-(benzofurane-2-yl)-2-[4-(5-cyano-1,2,3-[H]-triazole-4-yl-phenyl]-ethylene Among these, the compounds listed under a, c, f, g, k, and o are preferred.

In the same manner there are suitable as optical brighteners the N-methyl compounds of the formula (I), in particular those of the substances a to o, which are obtained, for example by the reaction of the products with dimethyl sulfate, as well as the correspondingg N-ethyl compounds obtained, for example by reaction with diethylsulfate. Among these the methylation and ethylation products of f, k and o are preferred.

The reaction products obtained by these alkylations constitute mixtures of the 3 possible isomers the chromatographic separation of which is possible (for example on silica gel with benzene or chloroform), but which is not necessary because the isomer mixtures may be used in the same manner as optical brighteners as the pure components.

As substrates to be brightened, there may be mentioned, for example the following materials: lacquers, natural and synthetic fibers, for example those made of natural or regenerated cellulose, acetyl cellulose, natural and synthetic polyamides, such as wool, polyamide-6 and -6.6, polyesters, polyolefines, polyvinylchoride, polyvinylidene chloride, polystyrene or polyacrylonitrile, as well as foils, films ribbons or bands or shaped bodies made of such materials.

The compounds of the invention which are insoluble in water may be used in the form of solutions in organic solvents or in the form of aqueous dispersions prepared advantageously with the aid of a dispersing agent. As dispersing agents there may be used, for example soaps, polyglycol ethers, which derive from fat alcohols, fatty amines or alkyl phenols, cellulose sulfite waste lyes or condensation products of naphthalene-sulfonic acid with formaldehyde which may be alkylated.

The compounds of the general formula (I) may also be added to detergents. These latter may contain the usual fillers and auxiliary substances such as alkali metal silicates, alkali metal phosphates and -polymetaphosphates, alkali metal borates, alkali metal salts of carboxy-methyl celluloses, foam stabilizers such as alkanol amides of higher fatty acids or complex formers such as soluble salts of ethylene-diamine-tetraacetic acid or diethylene triaminepentaacetic acid, as well as chemical regent agents such as perborates or percarbonates.

Brightening of the fibrous materials with the aqueous or optionally organic brighteners is carried out either according to the exhaust process at temperatures in the range of, preferably, about 20° to about 150° C, or under the conditions of the thermosol process, in which the textile material is impregnated or sprayed with the solution or dispersion of the optical brightener and squeezed between rollers to a residual moisture content of about 50 to about 120%. The textile material is then subjected for about 10 to about 300 sec. to a heat treatment, preferably with the aid of dry heat, at about 120° to about 240° C. This thermosol process may also be combined with other finishing operations, for example with a finishing process in order to improve the easycare properties.

Furthermore the compounds of the invention may be added to high molecular organic materials before or during their shaping. Thus, for example they may be added in the preparation of films, foils, bands or ribbons or shape bodies to the press masses or be dissolved in the spinning mass prior to spinning. Suitable compounds may also be added to low molecular starting materials prior to the polycondensation or polymerisation, as in the case of polyamide-6, polyamide-6.6 or linear esters of the type of the polyethyleneglycol terephthalate.

Compounds of the invention which are substituted by one or, preferably, 2 carboxy or carbalkoxy groups, may be bound to linear polyester molecules and synthetic polyamides by an ester or amide linkage, if they are added to these materials or preferably to the starting materials thereof, under suitable conditions. Optical brighteners fixed in this manner by a chemical linkage to the substrate are distinguished by an extraordinarily high fastness to sublimation and to solvents.

The quantity of the compounds of the general formula (I) to be used according to the invention, referred to the material to be optically brightened, may vary within wide limits depending on the field of applications and on the effect desired. It can easily be determined by preliminary tests and is in general between about 0.01 and about 2%.

The following examples illustrate the invention.

EXAMPLE 1 a. 1-p-Tolyl-2-cyano-2-phenylsulfonyl-ethylene (stage 1)

120 g (1 mole) of p-methylbenzaldehyde were heated to the boil on a water separator and under reflux with 181 g (1 mole) of phenylsulfonyl-acetonitrile in 500 ml benzene with addition of 6 ml of piperidine and 3 ml of glacial acetic acid. After 5 hours, 17 ml water had separated. Upon cooling to 10° C, the 1-p-tolyl-2-cyano-2-phenylsulfonyl-ethlene crystallized; after suction filtration, washing with 150 ml of cold benzene and drying, 206 g (73% of the theory) were obtained; melting point: 145°–147° C.

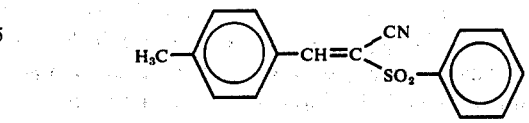

b. 1-(4-Bromomethylphenyl)-2-cyano-2-phenylsulfonyl-ethylene (stage 2)

56.8 g (0.2 mole) of 1-p-tolyl-2-cyano-2-phenylsulfonylethylene were dissolved in 1.000 ml of anhydrous carbon tetrachloride at 40° to 50° C. After addition of 35.6 g (0.2 mole) of N-bromosuccinimide and 1.2 g of dibenzoylperoxide, the whole was heated to the boil under reflux. After 5 hours, the mixture was filtered by still hot; as residue 17.2 g (about 86%) of succinimide melting at 125° C remained behind. The filtrate was evaporated on a rotary steamer and under the vacuum produced by a water jet and the residue was recrystallized from 400 ml of ethanol. 47.4 g (65 of the theory) of weakly yellow crystal melting at 120° to 122° C were isolated. Characteristical NMR-signal in CDCl$_3$/TMS: —CH$_2$Br at $\delta$ = 4.6 ppm.

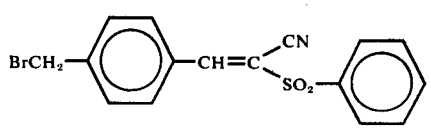

c.

1-(4-triphenylphosphoniummethylphenyl)-2-cyano-2-phenyl-sulfonyl-ethylene bromide (stage 3)

36.2 g (0.1 mole) of 1-(4-bromomethylphenyl)-2-cyano-2-phenylsulfonylethylene, dissolved in 150 ml of benzene, were mixed with 26.2 (0.1 mole) of triphenylphosphene, dissolved in 50 ml of benzene and the whole was stirred for 24 hours at room temperature, and then for 2 hours at 40° C. After cooling the product was filtered off with suction and washed with benzene. 52.6 g (84% of the theroy) of the colorless phosphonium salt having a melting point of 285° to 289° C were obtained.

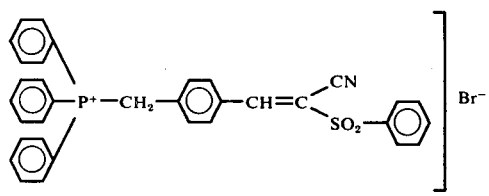

d. 1-(stilbene-4-yl)-2-cyano-2-phenylsulfonylethylene (stage 4)

12.48 g (20 mmole) of the triphenylphosphonium bromide of Example 1 c) were dissolved in 200 ml of absolute dimethylformamide at 70° C, by stirring and under an atmosphere of nitrogen. After the mixture had cooled to 30° to 35° C, 2.24 g (20 mmole) of potassium-tert. butylate were introduced and the whole was stirred again for 5 minutes. The solution of 2.12 g (20 mmole) of benzaldehyde in 20 ml of absolute dimethylformamide was added dropwise within 10 minutes to the violet solution and the whole was further heated for 4 hours to 100° C under an atmosphere of nitrogen. After cooling, the potassium bromide separated was filtered off with suction and the dimethylformamide was eliminated by destillation on a rotary vaporator and under a vacuum produced by a water jet. The residue was combined with 200 ml of hot ethanol. After cooling, 4.65 g of weakly yellow crystals of 1-(stilbene-4-yl)-2-cyano-2-phenylsulfonylethylene having a melting point of 179° to 183° C (corresponding to a yield of 63% of the theory), were obtained.

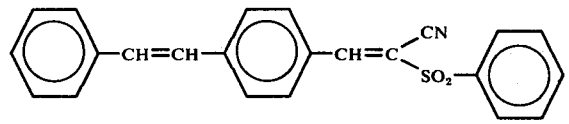

e. 4-(stilbene-4-yl)-5-cyano-1,2,3-[H]-triazole (stage 5)

715 mg (11 mmole) of sodium azide were introduced at 60° C into the solution of 3.71 g (10 mmoles) of the 1-(stilbene-4-yl)-2-cyano-2-phenylsulfonylethylene from Example 1(d) in 20 ml of absolute dimethylformamide. The whole was heated for 3 hours to 100° C. The yellow colour of the starting product rapidly disappeared and samples taken from the reaction mixture showed a strong fluorescence when illuminated with light having a wave length of 350 nm. The mixture was allowed to cool and poured into 200 ml of water; upon weak acidification with 2 n HCl or dilute acetic acid the triazole recipitated in crystalline form. 2.7 g of 4-(stilbene-4-yl)-5-cyano-1,2,3-[H]-triazole were obtained (corresponding to about 100% of the theory); melting point 190° to 192° C. Absorption in DMF:λmax. 342 nm.

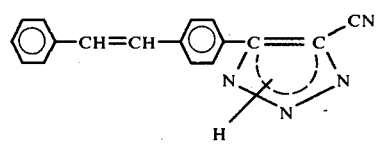

EXAMPLES 2 to 19

In a manner analogous to that described in Example 1 for the 4-(stilbene-4-yl)-5-cyano-1,2,3-[H]-triazole, there were obtained, as examples 2 to 19 (c.f. the following table I) the corresponding 5-cyano-triazoles of the formula I by using the mono- and bi-functional aldehydes (A'—CHO or OHC—A"—CHO) in step 4 of the synthesis (Example 1 (d)) instead of the benzaldehyde. Working up (in particular the measure for separating the main side product triphenylphosphine oxide) in step 4 depends on the properties for the phenylsulfonyl-ethylenes obtained. In this respect the following processes are used:

a. sparingly soluble phenylsulfonyl-ethylenes crystallize upon cooling already in the dimethylformamide solution;

b. In most cases the product is isolated by evaporation of the dimethylformamide under a vacuum produced by a water jet and dissolution of the residue in hot ethanol; on cooling the phenylsulfonylethylene crystallizes.

c. In some cases in the working up according to (b), the phenyl-sulfonylethylenes are unsoluble in ethanol; the residue is then boiled up several times with ethanol.

d. If the phenylsulfonylethylene does not precipitate in crystalline form when worked up according to method (b), the oily product is subjected to a purification by column chromatography.

e. Further purification of the phenylsulfonylethylenes is possible by recrystallization from polar solvents such as ethanol or dioxane or a mixture of ethanol/dioxane/water.

Purification of the triazoles (prepared in a manner analogous to step 5, example 1) is possible by recrystallization from polar solvents or mixtures with water, optionally by chromatography on silica gel.

Table I

Phenylsulfonylethylenes (step 4) and triazoles (step 5) prepared in a manner analogous to that described in example 1.

| Example No. | aldehyde A'—CHO or dialdehyde OHC—A''—CHO used | phenylsulfonyl-ethylene Fp. (°C) | Th. yield (%) | triazole Fp. (°C) | Th. yield (%) | absorption in DMF max (nm) |
|---|---|---|---|---|---|---|
| 2 | CH₃—C₆H₄—CHO (para) | 174–6 | 58 | 204–5 | 100 | 378 |
| 3 | CH₃O—C₆H₄—CHO (para) | 176–8 | 77 | 217–8 | 100 | 347 |
| 4 | 3,4,5-(CH₃O)₃—C₆H₂—CHO | 167–9 | 85 | 237–40 | 99 | 349 |
| 5 | Cl—C₆H₄—CHO (para) | 181–3 | 77 | 241–4 | 100 | 344 |
| 6 | Cl—C₆H₄—CHO (meta) | 248–51 | 82 | 235–7 | 72 | 346 |
| 7 | CH₃O—C(O)—C₆H₄—CHO | 232–3 | 78 | 227–30 | 81 | 358 |
| 8 | NC—C₆H₄—CHO | 210–30 | 86 | 275–8 | 78 | 358 |
| 9 | (H₃C)₂N—C₆H₄—CHO | 90–5 | 97 | 95–127 | 97 | 370 |
| 10 | biphenyl-CHO | 196–200 | 79 | 264–6 | 66 | 353 |
| 11 | 3-(4-formylphenyl)coumarin | 290–2 | 51 | 305–9 | 100 | 368 |
| 12 | 2-(4-formylphenyl)benzoxazole | 287–8 | 86 | 289–91 | 88 | 372 |
| 13 | 2-methoxy-1-naphthaldehyde | 158–60 | 16 | 79–91 | 100 | 359 |
| 14 | 4-methoxy-1-naphthaldehyde | 176–80 | 87 | 80–114 | 92 | 359 |
| 15 | pyridine-CHO | 218–20 | 81 | >300 | 77 | 343 |
| 16 | thiophene-2-CHO | 163–5 | 78 | 198–200 | 76 | 354 |

Table I-continued

Phenylsulfonylethylenes (step 4) and triazoles (step 5) prepared in a manner analogous to that described in example 1.

| Example No. | aldehyde A'—CHO or dialdehyde OHC—A''—CHO used | phenylsulfonylethylene Fp. (° C) | Th. yield (%) | triazole Fp. (° C) | Th. yield (%) | absorption in DMF max (nm) |
|---|---|---|---|---|---|---|
| 17 | ![structure with phenyl, O, CHO] | 222–4 | 76 | 231–3 | 97 | 364 |
| 18 | OHC—⟨phenyl⟩—CHO | 92–105 | 62 | >300 | 21 | 386 |
| 19 | OHC—⟨phenyl⟩—⟨phenyl⟩—CHO | 245–70 | 100 | 238–70 | 87 | 367 |

The bis-compounds obtained according to examples (18) and (19) have the formulae Absorption in DMF:$\lambda_{max}$331 nm. The product was found to be a mixture of the 3 possible isomers.

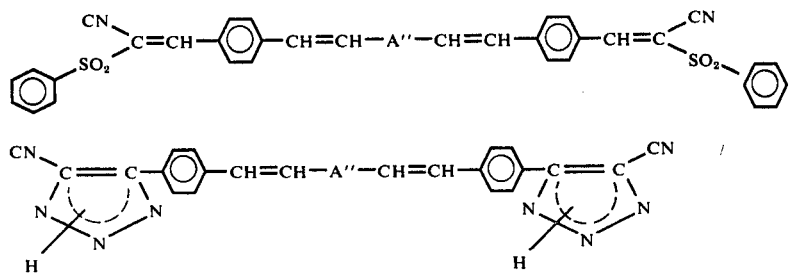

EXAMPLE 20

4-(stilbene-4-yl)-5-cyano-N-methyl-1,2,3-[H]-triazole 0.68 g (2.5 mmoles) of 4-(stilbene-4-yl)-5-cyano-1,2,3-[H]-triazole obtained according to example 1 (e) were dissolved in 20 ml of 1n sodium hydroxide solution with addition of 5 ml of acetone. 750 mg (6 mmole) dimethylsulfate were added and the whole was stirred for 5 hours at room temperature. The crystals that had separated were filtered off with suction and, after drying, 520 mg of 4-(stilbene-4-yl)-5-cyano-N-methyl-1,2,3-[H]-triazole melting at 99° to 106° C, corresponding to 73% of the theory, were obtained

EXAMPLES 21 to 31

In a manner analogous to that described in example 20 there were obtained other N-methyl-triazoles by methylation of the triazoles prepared in examples 2 to 19. The melting points of the crude products were in the most cases unsharp, since they were mixtures of the three possible isomers which also resulted of the nucluar resonance spectra of the substances. The N-methyltrazoles prepared in this manner are indicated in the following table II and the properties of the individuel isomers (I, II, III) are indicated as far as these have been separated by column chromatography. The yields of crude product are in general between 80 and 100% of the theory.

Table II

N-methyl-triazoles from triazoles of table I by methylation.

| Example No. | starting triazole example no. of table I | isomeres from raw product type | Fp.(° C) | Th. yield (%) | Absorption max. in DMF (nm) |
|---|---|---|---|---|---|
| 21 | 2 | I | 151–3 | 18 | 336 |
| 22 | 5 | I | 144–6 | 38 | 336 |
|  |  | II | 200–4 | 13 | 338 |
| 23 | 6 | I+II+III | 145–63 | 43 | 331 |
| 24 | 8 | I | 192–3 | 12 | 342 |
|  |  | II | 260–2 | 6 | 343 |
| 25 | 9 | I+II+III | 115–30 | 15 | 383 |
| 26 | 10 | I | 206–9 | 32 | 347 |
|  |  | II | 269–73 | 3 | 352 |
|  |  | III | 179–87 | 1 | 342 |
| 27 | 11 | I | 193–203 | 5 | 358 |
| 28 | 12 | I | 272–5 | 47 | 363 |
|  |  | I+II+III | 282–95 | 7 | 363 |
| 29 | 14 | I | 161–5 | 14 | 366 |
|  |  | II | 232–5 | 5 | 369 |
| 30 | 16 | I | 140–1 | 28 | 348 |

Table II-continued

N-methyl-triazoles from triazoles of table I by methylation.

| Example No. | starting triazole example no. of table I | isomeres from raw product type | Fp.(° C) | Th. yield (%) | Absorption max. in DMF (nm) |
| --- | --- | --- | --- | --- | --- |
|  |  | II | 204–8 | 4 | 352 |
| 31 | 17 | I | 200–1 | 13 | 358 |
|  |  | II | 242–3 | 5 | 360 |

EXAMPLE 32

4-[4'-(benzoxazole-2-yl)-stilbene-4-yl]-5-cyano-N-ethyl-1,2,3-[H]-triazole 3.9 g (10 mmole) of 4-[4'-(benzoxazole-2-yl)-stilbene-4-yl]-cyano-1,2,3-[H]-triazole were dissolved in 75 ml of 0.4 N-sodium hydroxide solution with the addition of 180 ml of aceton. After addition of 4.6 g (30 mmole) of diethylsulfate while stirring at room temperature, a light yellow crystalline precipitate separated after about 30 minutes. Stirring was continued for about 24 hours, the whole was filtered with suction and dried. 3.4 g of crude product (82% of the theory) were obtained which were found to melt at 216° to 218° C after recrystallization in dioxane. Absorption: in DMF:$\lambda_{max}$ 363 nm.

EXAMPLE 33 a.

4,4'-bis-[(2-cyano-2-phenylsulfonyl)-ethene-1-yl]-stilbene (VII)

1.18 g (5 mmole) of stilbenzdialdehyde, 1.81 g (10 mmoles) of phenyl-sulfonylacetonitrile, 0.7 ml of glacial acetic acid and 0.25 g of ammonium acetate were heated together in 100 ml of benzene on a water separator for 3 hours to the boil under reflux; 0.35 ml of water were separated. Upon cooling, the crystals that had separated were isolated. By concentration of the filtrate, a second fraction was obtained. Together 2.81 g of 4,4'-bis-[(2-cyano-2-phenylsulfonyl)-ethene-1-yl]-stilbene melting at 306° to 310° C, corresponding to a yield of 100%, were isolated.

b. 4,4'-bis-(5-cyano-1,2,3-[H]-triazole-4-yl)-stilbene (IX)

2.81 g (5 mmoles) of 4,4'-bis-[(2-cyano-2-phenylsulfonyl)-ethene-1-yl]-stilbene were suspended in 20 ml of dimethylformamide and heated to 100° C. 715 mg (11 mmoles) of sodium acide were added and the whole was stirred at 2 hours at 100° C. After cooling to room temperature 100 ml of water were added and the whole was acidified weakly with 2 N—HCl. The 4,4'-bis(5-cyano-1,2,3-[H]-triazole-4-yl)-stilbene was obtained which could be purified by dissolution in sodium hydroxide solution and precipitation with hydrochloric acid. Yield of purified substance: 1.4 g of product having a melting point of 320° C, and corresponding to 77% of the theory.

Absorption maximum in DMF: 341 nm.

EXAMPLE 34

4,4'-bis-(5-cyano-N-methyl-1,2,3-[H]-triazole-4-yl)-stilbene (X)

1.0 g (2.75 mmoles) of 4,4'-bis-(5-cyano-1,2,3-[H]-triazole-4-yl)-stilbene were dissolved in 25 ml of 1.6 N-sodium hydroxide solution. 1.3 g (10 mmoles) of dimethylsulfate were added and the whole was stirred for 2 hours at room temperature and subsequently for 1 hour at 70° C. After cooling, the product that had precipitated was filtered off with suction and 0.7 g of 4,4'-bis-(5-cyano-N-methyl-1,2,3-[H]-triazole-4-yl)-stilbene melting at 125° C (decomposition) (corresponding to 65% of the theory) was obtained.

Absorption maximum in DMF: 363 nm.

EXAMPLE 35

A fabric of polyethylene terephthalte was impregnated with a bath containing, in dispersed form, 1 g/l of the optical brightener obtained according to example (28). The material so treated was squeezed with rollers until it had only 60% of its dry weight of liquid and then submitted to a hot air treatment at 180° C for 30 sec. After the treatment the fabric had a white degree according to Berger of 139% ($Wg = Y + 3 (Rz - Rx)$).

In addition the fabric showed an excellent fastness to light of 6 to 7 (measured according to DIN 54 004).

EXAMPLE 36

A yarn of polyethylene terephthalate was introduced into a bath at a ratio of 1:25, containing 0.088% of the optical brightener obtained according to example (28). The cold bath was heated within 30 minutes to 120° C and then allowed to dwell at this temperature for 30 minutes. After rinsing and drying, the yarn showed an excellent violetish white degree of 132% (according to Berger). The fastness to light was found to be 6 to 7.

EXAMPLE 37

2-[4'-benzoxazole-2-yl-stilbene-4-yl)-5-cyano-1,2,3-triazole-N-yl]-methylacetate 3.9 g (10 mmoles) of 4-(4'-benzoxazole-2-yl-stilbene-4-yl)-5-cyano-1,2,3-[H]-triazole, obtained according to example 12, and 1 g (10 mmoles) of tris-isopropanolamine were dissolved in 250 ml of absolute DMF under an atmosphere of nitrogen, combined with 2.2 g (20 mmoles) of chloroformic acid methyl ester and the whole was stirred for 4 hours at 100° C. After cooling, 600 ml of ice-water were added, the whole was acidified with 2 N-acetic acid, filtered up with suction, washed with methanol and dried. 3.9 g (85% of the theory) of a colorless powder of 2-[4-(4'-benzoxazole-2-yl-stilbene-4-yl)-5-cyano-1,2,3triazole-N-yl]-acetic acid methylester were obtained which after double recrystallization from a mixture of dioxane/bleaching earth had a melting point of 248° to 249° C.

Absorption: $\lambda_{max} = 363$ nm. $\epsilon = 7.14 \times 10^4$

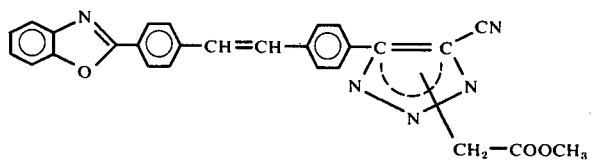

In a manner analogous to that described above the following compounds indicated in the table III were prepared:

Table III

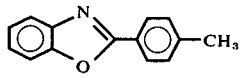

| R | Fp. (° C) | yield % | Absorption in DMF max(nm) |
|---|---|---|---|
| —CH$_2$—C$_6$H$_5$ | 244–245 | 55 | 363 |
| —CH$_2$CN | 257–258 | 42 | 364 |

EXAMPLE 38 a. 2-p-tolyl-benzoxazole 68 g (0.5 mole of p-toluic acid were heated with 54.5 g (0.5 mole) of p-aminophenol and 2 g of boric acid in 750 ml of 1,2-methylnaphthalene and the water that formed was eliminated slowly by azeotropic destillation. After heating for 6 hours, 1 g of boric acid were added. After 12 hours, 16 ml of H$_2$O (98%) passed over. The solvent was then removed until dryness, the residue was dissolved in 750 ml of ethanol, clarified with silica gel while still hot, and combined after filtration, while still hot, with 500 ml of H$_2$O. After cooling and filtration with suction at room temperature and washing with aqueous ethanol, there were obtained 89.4 g (85.6% of the theory) of 2-p-tolyl-benzoxazole melting at 113° to 114° C.

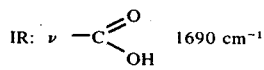

b. 4-(p-chlorophenylimino-methyl)-benzoicacid methyl ester 165 g (1 mole) of 4-carbomethoxybenzaldehyde and 128 g (1 mole) of 4-chloroaniline were stirred in 2500 ml of ethanol for 3 hours on a weak reflux, when cooled to −10°C, filtered with suction and washed with ethanol having a temperature of −10° C. After drying, 227 g (83% of the theory) of 4-(p-chlorophenylimino-methyl)-benzoicacid methyl ester of the following formula were obtained

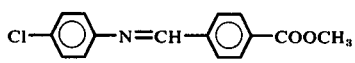

c. 4-(4'-benzoxazole-2-yl)-stilbene-carboxylic acid 20.9 g (0.1 mole) of 2-p-tolylbenzoxazole and 27.3 g (0.1 mole) of 4-(p-chlorophenylimino-methyl)-benzoic acid methyl ester were stirred with 56 g (0.5 mole) of potassium-tert.-butylate in 750 ml of anhydrous DMF for 1 hour at room temperature under an atmosphere of nitrogen, combined with 60 ml of concentrated hydrochloric acid, boiled up and filtered in a funnel while hot. The filtrate was cooled to 0° C, filtered with suction and washed with methanol. 23.6 g (69% of the theory) of 4-(4'-benzoxazole-2-yl)-stilbene-carboxylic acid having a melting point of 310° C were obtained which could be further reacted without purification.

IR: $\nu$ —C(=O)OH  1690 cm$^{-1}$

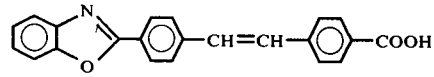

d. 4-(4'-benzoxazole-2-yl)-stilbene-carboxcylic acid chloride 3.4 g (10 mmoles) of 4-(4'-benzoxazole-2-yl)-stilbene-carboxylic acid were heated in 50 ml of thionyl with 3.6 g (30 mmoles) of thionylchloride and 0.1 ml of DMF for 5 hours under reflux. After cooling, the product was filtered off with suction under an atmosphere of hydrogen and washed with xylene. After drying, 3.3 g (92% of the theory) of 4-(4'-benzoxazole-2-yl)-stilbene-carboxcylic acid were obtained.

IR: $\nu$ —C(=O)Cl  1770 cm$^{-1}$

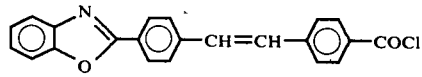

In view of the fact that the acid chloride was very sensitive to hydrolysis, it was found to be advantageous to work it up in its xylene-wet state without further purification.

e. 1-(stilbene-4-yl-4'-benzoxazole-2-yl)-2-cyano-2-phenylsulfonyl-ethylene 3.3 g (9.2 mmoles) of the carboxcylic acid chloride of example (d) were heated in 200 ml of xylene with 0.7 g of a hydrogenation catalyst (5% of Pd on BaSO$_4$) and 7 mg of quinoline S (for poisoning the catalyst). Hydrogen was introduced in a strong stream at 120° C, while stirring intensively, and the hydrochloric acid that had formed was titrated continuously. After consumption of the theoretical amount of 9.2 ml of 1 N—-

NaOH, the hydrogen was replaced by nitrogen and the whole was freed from catalyst by filtration while hot.

The filtrate with combined, without isolation of the aldehyde, with 1.8 g (10 mmoles) of phenylsulfonyl-acetonitrile, 0.1 ml of piperidine and 0.05 nl of glacial acetic acid, boiled for 1 hour at the water separator, 80 ml of xylene were removed by distillation and then the product was filtered off at 80° C. 3.7 g (75.7% of the theory) of 1-(stilbene-4-yl-4'-benzoxazole-2-yl)-2-cyano-2-phenylsulfonyl-ethylene melting at 277° to 278° C were obtained,

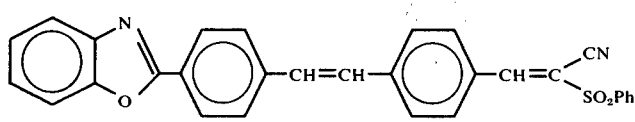

which could be reacted to the triazole with further purification in a manner analogous to that described in example (12) with Na-azide.

f.
4-(4'-benzoxazole-2-yl-stilbene-4-yl)-5-cyano-N-methyl-1,2,3-triazole 4.9 g (10 mmoles) of 1-(stilbene-4-yl-4'-benzoxazole-2-yl)-2-cyano-2-phenylsulfonyl-ethylene were suspended in 100 ml of absolute dimethylformamide under an atmosphere of nitrogen, combined at 40° C, portionwise, with 0.7 g (11 mmoles) of sodium azide and the solution was stirred for 4 hours at 100° C. It was then cooled to 32° C, 2.5 g (20 mmoles) of dimethylsulfate were added and the mixture was further stirred for 3 hours. It was then clarified at the boiling temperature with active carbon, filtered while still hot and the filtrate combined with 200 ml of acetonitrile. After having allowed to cool to room temperature, it was suction-filtered, the product was washed with methanol, water and dried. 1.9 g (47%) of 4-(4'-benzoxazole-2-yl-stilbene-4-yl)-5-cyano-N-methyl-1,2,3-triazole were obtained which, after recrystallization from dioxane/bleaching earth, had a melting point of 264° to 266° C.

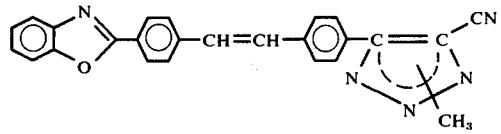

We claim:
1. A compound of the formula

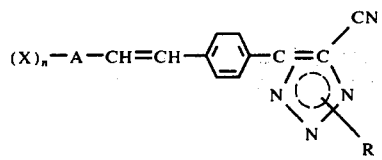

wherein R is hydrogen, or lower alkyl which may be substituted by phenyl, hydroxy, lower carbalkoxy or cyano
A is a group of the formula

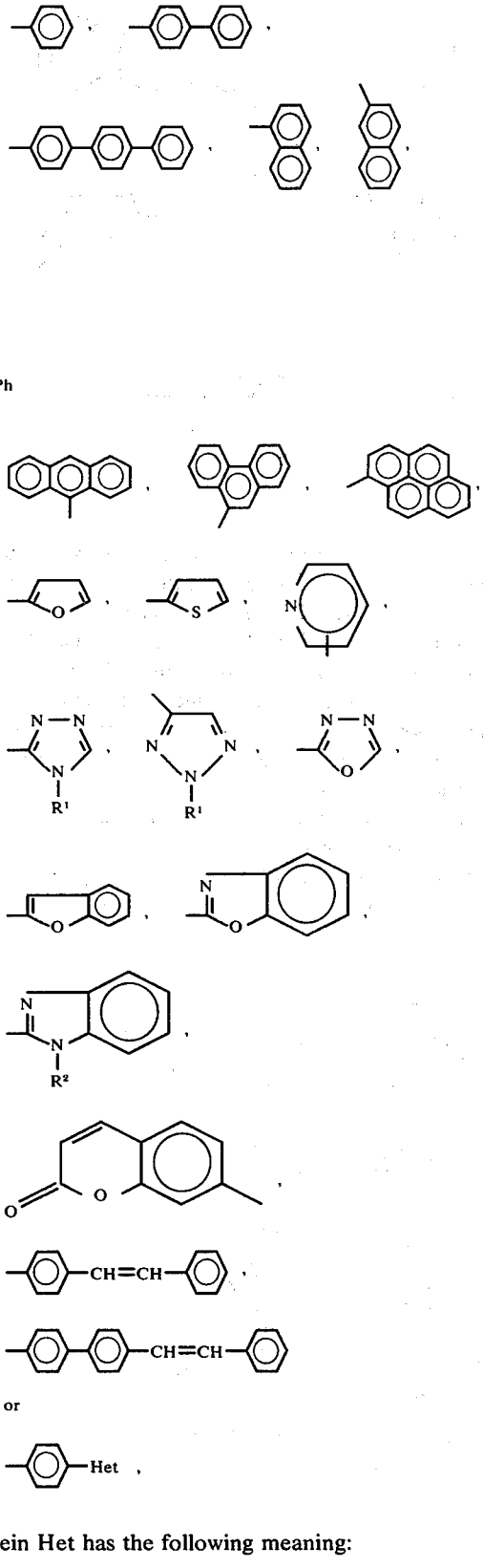

or

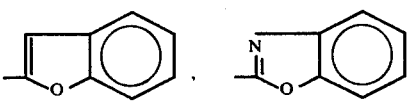

wherein Het has the following meaning:

-continued

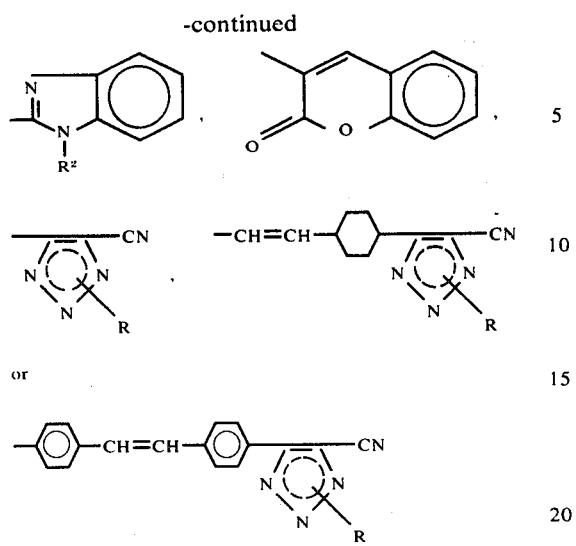

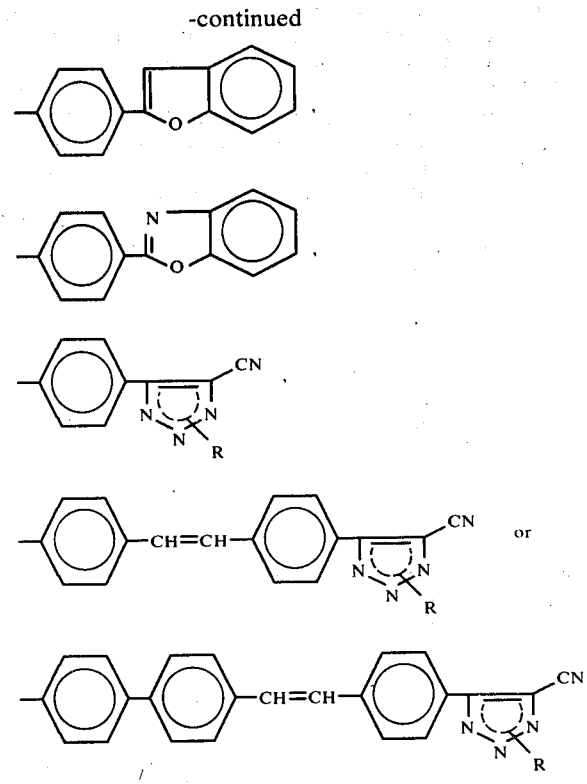

X is hydrogen or identical or different non-chromophorous groups of the series of fluorine, chlorine or bromine atoms, lower alkyl, lower alkoxy, amino, lower mono- or di-alkyl amino, lower trialkyl ammonium or acyl amino groups, or carboxy or sulfo which may be functionally modified, and 2 adjacent radicals X may together also represent a lower alkylene or an 1,3-dioxypropylene group, $n$ is an integer from 1 to 3, $R^1$ is hydrogen, lower alkyl or phenyl, and $R^2$ is hydrogen or lower alkyl.

2. A compound as claimed in claim 1, wherein R is hydrogen, methyl or ethyl, A is a group of the formula

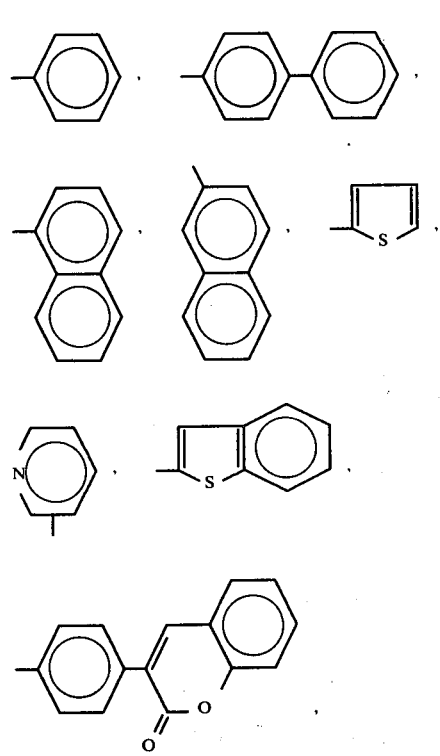

X is hydrogen, chlorine, methyl, methoxy, cyano, carboxy, lower carbalkoxy, amino, lower mono- or dialkyl-amino or lower alkanoyl-amino or benzoyl-amino, and $n$ is 1 to 3.

3. A compound as claimed in claim 1 wherein A is a group of the formula

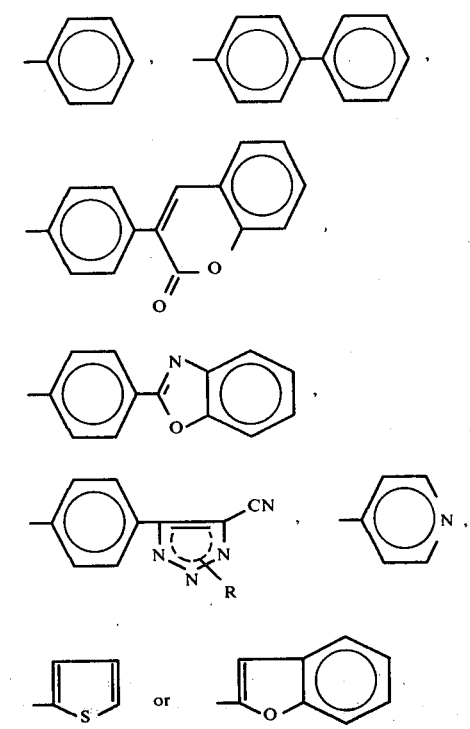

X is hydrogen, chlorine, methyl, methoxy, cyano or lower carbalkoxy, n is 1 to 3, and R is hydrogen, methyl or ethyl.

4. The compound as claimed in claim 1 which is 4-(stilbene-4-yl)-5-cyano-1,2,3-[H]-triazole.

5. The compound as claimed in claim 1 which is 4-(4'-methoxy-stilbene-4-yl)-5-cyano-1,2,3-[H]-triazole.

6. The compound as claimed in claim 1 which is 4-(4'-chlorostilbene-4-yl)-5-cyano-1,2,3-[H]-triazole.

7. The compound as claimed in claim 1 which is 4-(4'-methoxy-carbonyl-stilbene-4-yl)-5-cyano-1,2,3-[H]-triazole.

8. The compound as claimed in claim 1 which is 4-[4'-(benzoxazole-2-yl)-stilbene-4-yl]-5-cyano-1,2,3-[H]-triazole.

9. The compound as claimed in claim 1 which is 1-(benzofurane-2-yl)-2-[H]-triazole-4-yl)-phenyl]-ethylene.

* * * * *